(12) United States Patent
Hessler et al.

(10) Patent No.: US 9,706,993 B2
(45) Date of Patent: Jul. 18, 2017

(54) STAPLE CARTRIDGE WITH SHIPPING WEDGE

(71) Applicant: Covidien LP, Mansfield, MA (US)

(72) Inventors: Thomas Hessler, Bethel, CT (US); Stanislaw Kostrzewski, Newtown, CT (US); Ernest Aranyi, Easton, CT (US)

(73) Assignee: Covidien LP, Mansfield, MA (US)

( * ) Notice: Subject to any disclaimer, the term of this patent is extended or adjusted under 35 U.S.C. 154(b) by 656 days.

(21) Appl. No.: 14/159,012

(22) Filed: Jan. 20, 2014

(65) Prior Publication Data

US 2014/0252065 A1    Sep. 11, 2014

Related U.S. Application Data

(60) Provisional application No. 61/774,942, filed on Mar. 8, 2013.

(51) Int. Cl.
| | |
|---|---|
| *A61B 17/068* | (2006.01) |
| *A61B 17/072* | (2006.01) |
| *A61B 17/00* | (2006.01) |
| *A61B 90/00* | (2016.01) |

(52) U.S. Cl.
CPC ........ *A61B 17/0682* (2013.01); *A61B 17/072* (2013.01); *A61B 17/07207* (2013.01); *A61B 2017/0053* (2013.01); *A61B 2017/00398* (2013.01); *A61B 2017/00477* (2013.01); *A61B 2017/00734* (2013.01); *A61B 2017/0688* (2013.01); *A61B 2017/07271* (2013.01); *A61B 2090/038* (2016.02); *Y10T 29/4973* (2015.01); *Y10T 29/49821* (2015.01)

(58) Field of Classification Search
None
See application file for complete search history.

(56) References Cited

U.S. PATENT DOCUMENTS

| | | | |
|---|---|---|---|
| 4,892,244 | A | 1/1990 | Fox et al. |
| 5,065,929 | A | 11/1991 | Schulze et al. |
| 5,366,133 | A | 11/1994 | Geiste |
| 5,415,335 | A | 5/1995 | Knodell, Jr. |
| 5,762,255 | A | 6/1998 | Chrisman et al. |
| 7,097,089 | B2 | 8/2006 | Marczyk |
| 7,143,924 | B2 | 12/2006 | Scirica et al. |

(Continued)

FOREIGN PATENT DOCUMENTS

| | | |
|---|---|---|
| EP | 2462875 A2 | 6/2012 |
| EP | 2529673 A2 | 12/2012 |

OTHER PUBLICATIONS

European Search Report dated Oct. 7, 2014 issued in European Appln. No. 14158241.

(Continued)

*Primary Examiner* — Michelle Lopez
*Assistant Examiner* — Chinyere Rushing-Tucker

(57) ABSTRACT

An end effector usable with a surgical instrument includes a first jaw pivotably coupled to a second jaw. The first jaw includes staple forming depressions. A staple cartridge is releasably attachable to a channel of the second jaw. A plurality of staples is disposed in the staple cartridge. A shipping wedge is releasably attached to the staple cartridge. The shipping wedge maintains the staples in their respective retention slots and is usable to separate the staple cartridge from the channel of the second jaw.

20 Claims, 17 Drawing Sheets

(56) References Cited

U.S. PATENT DOCUMENTS

| | | |
|---|---|---|
| 7,225,963 B2 | 6/2007 | Scirica |
| 7,780,055 B2 | 8/2010 | Scirica et al. |
| 8,225,979 B2 | 7/2012 | Farascioni et al. |
| 8,397,972 B2 | 3/2013 | Kostrzewski |
| 2005/0222616 A1* | 10/2005 | Rethy .............. A61B 17/07207 606/215 |
| 2007/0167960 A1 | 7/2007 | Roth et al. |
| 2008/0083807 A1 | 4/2008 | Beardsley et al. |
| 2012/0145714 A1* | 6/2012 | Farascioni ........... A61B 17/072 220/260 |
| 2012/0241499 A1 | 9/2012 | Baxter, III et al. |
| 2013/0306703 A1 | 11/2013 | Ehrenfels et al. |

OTHER PUBLICATIONS

European Search Report dated Mar. 2, 2016, issued in European Application No. 15196602.
Chinese Office Action dated Apr. 13, 2017, issued in Chinese Appln. No. 201410079812X.

\* cited by examiner

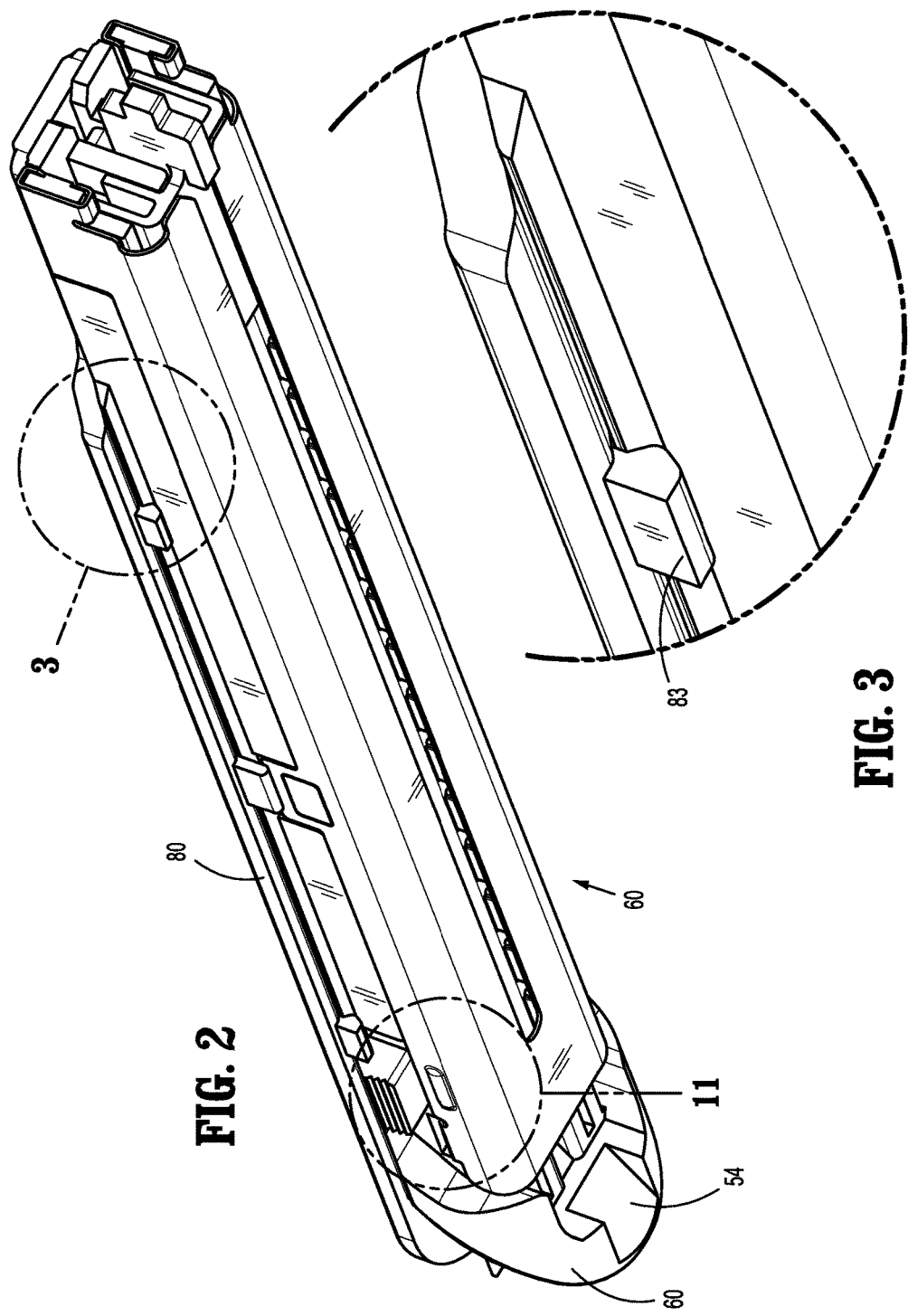

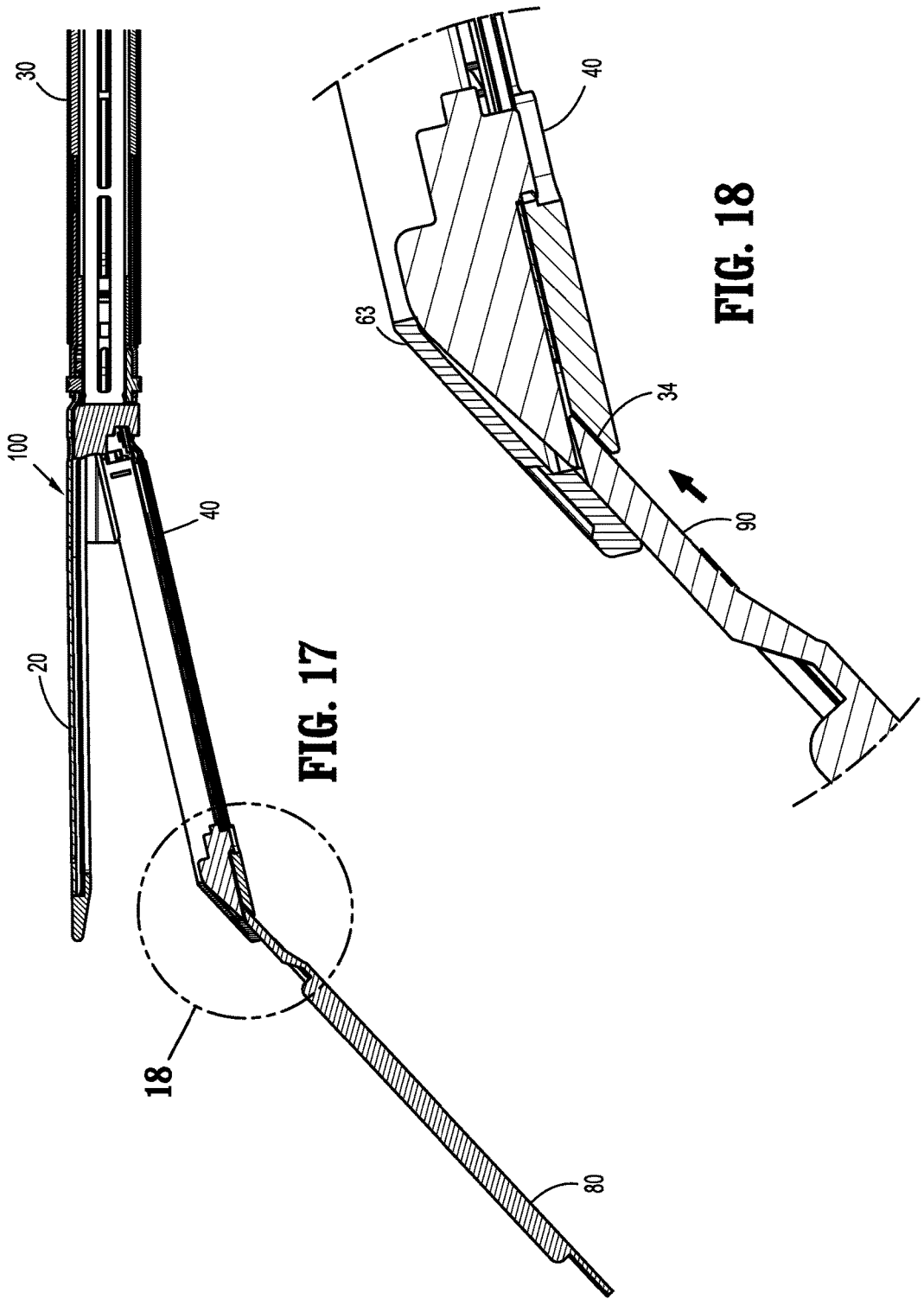

STAPLE CARTRIDGE WITH SHIPPING WEDGE

CROSS-REFERENCE TO RELATED APPLICATIONS

This application claims the benefit of and priority to U.S. Provisional Patent Application No. 61/774,942, filed Mar. 8, 2013, the entire disclosure of which is incorporated by reference herein.

BACKGROUND

1. Technical Field

The present disclosure relates to a staple cartridge for use with a surgical instrument. More particularly, the present disclosure relates a staple cartridge with a shipping wedge for maintaining a plurality of surgical fasteners in the staple cartridge and for separating the staple cartridge from a cartridge housing of the surgical instrument.

2. Background of Related Art

Surgical devices for applying surgical fasteners to tissue are well known. Endoscopic surgical devices for applying staples, clips or other fasteners include a handle assembly for actuating the device, an endoscopic shaft, and a tool assembly at the distal end of the endoscopic shaft. Certain of these devices are designed for use with replaceable loading units housing the staples or fasteners. For example, in using an endoscopic linear stapler, the user may select a loading unit with staples of a selected size and arranged in one or more lines of staples having a selected staple line length. After firing, the user may remove the loading unit, select another loading unit of the same or different size, and fire staples from the instrument again. Endoscopic surgical staplers having four lines of staples, arranged in pairs on either side of a cut line, are known.

Loading units in the form of replaceable cartridges are known. By contrast, other devices have loading units having a tool assembly, including a cartridge, anvil, drive assembly and knife are known. Such loading units have the benefit of providing a new knife with each loading of the loading unit.

Various surgical procedures are performed with surgical instruments having disposable or replaceable loading units. These loading units generally include a movable part or parts positioned to engage a drive member of a surgical instrument. If the moving part is not properly retained in position prior to and during attachment of the loading unit to a surgical instrument, the loading unit may not properly engage the surgical instrument and, thus, may not function properly. Some surgical instruments are provided with automatic locking systems which block movement of the components of the tool assembly prior to attachment to a surgical instrument and allow free movement of the movable parts of the tool assembly once the loading unit has been properly positioned on the surgical instrument.

SUMMARY

An end effector having first and second jaws is disclosed herein. The first jaw includes staple forming depressions and is pivotable with respect to the second jaw. The second jaw has a generally U-shaped channel defined by opposing sidewalls and a bottom surface. A pair of opposed recesses are located in a distal portion of the channel. Additionally, each of the opposed sidewalls includes a slot in a distal portion of the channel. An extension extends distally from the distal end of the second jaw and the extension includes a sloped surface.

A staple cartridge is releasably coupled to the second jaw and the staple cartridge includes opposed sidewalls. Each sidewall has a rail that extends along the sidewall and is parallel to a longitudinal axis of the staple cartridge. Each rail also protrudes outwardly from its respective sidewall. The staple cartridge includes a plurality of tissue contacting surfaces that are arranged in a stepped configuration. Each tissue contacting surface includes a plurality of retention slots having openings extending through the respective tissue contacting surfaces. The retention slots include a corresponding number of staples and pushers. The pushers slidably interact with a sled that is translatable between a proximal end of the staple cartridge and a distal end of the staple cartridge in response to actuation of a drive mechanism in a surgical instrument that is coupled to the end effector. A knife slot extends along a central longitudinal axis of the staple cartridge and is configured to allow proximal and distal translation of a knife. A pair of opposing protrusions is located near the distal end of the staple cartridge and releasably engages the recesses of the channel. Additionally, the staple cartridge includes opposed tabs near the distal end that are insertable into the notches of the staple cartridge for aligning the staple cartridge within the channel of the second jaw. A nose of the staple cartridge includes a recess that is aligned with the sloped surface of the second jaw when the staple cartridge is fully seated in the channel. A gap is defined by the recess of the nose and the sloped surface.

A shipping wedge is releasably attachable to the staple cartridge for maintaining the staples in their respective retention slots. The shipping wedge includes opposing top and bottom surfaces with a tongue extending from a distal end of the shipping wedge. The tongue includes a tapered surface and a distal tip. A plurality of tabs extends from the bottom surface of the shipping wedge and a central keel is attached to the bottom surface of the shipping wedge. Each tab has an outer surface, an inner surface, a planar bottom surface, and an inwardly extending protrusion. Each tab is flexibly and resiliently attached to the shipping wedge and releasably engages the rails of the staple cartridge.

According to one aspect of the present disclosure, an end effector for a surgical instrument includes a first jaw having a channel, a second jaw pivotably coupled to the first jaw, a staple cartridge positioned in the channel, and a shipping wedge releasably attached to the staple cartridge. The shipping wedge having a tongue extending from one end thereof, the tongue engageable with a distal portion of the staple cartridge and a distal portion of the first jaw such that manipulating the shipping wedge separates the staple cartridge from the first jaw. The tongue may have a tapered configuration and the first jaw may have a recess for receiving the tongue. The first jaw may have a generally U-shaped configuration with opposing sidewalls and each sidewall may include a rib extending along a portion of its length. The shipping wedge may have a plurality of tabs and each tab may be configured for releasably engaging the ribs of the second jaw. The shipping wedge may maintain a uniform distance between the first and second jaws. The shipping wedge may have a keel that is disposed in a channel of the staple cartridge. The keel may align the shipping wedge and the staple cartridge. The keel may inhibit translation of an actuation member through the channel. The keel may also have surface features that attach the shipping wedge to the staple cartridge. The shipping wedge may maintain surgical fasteners in their respective retention slots. The staple cartridge may have opposed sidewalls and each sidewall may include a knob extending therefrom such that the knobs may be received in recesses formed in the distal portion of the first jaw. The engagement of the knobs and the recesses may maintain the staple cartridge in the first jaw. A gap may be defined between the distal portion of the staple cartridge and the distal portion of the second jaw member such that the tongue of the shipping wedge may be inserted into the gap.

In certain embodiments, a sloped surface is formed at the distal end of the second jaw member. The sloped surface can extend from an external bottom surface of the second jaw member and leads angularly to an interior surface of the second jaw member.

In any of the embodiments disclosed herein, the shipping wedge can have a stepped shape.

In a further aspect of the present disclosure, a method of removing a staple cartridge from a stapling instrument includes the steps of separating a shipping wedge from a staple cartridge, the staple cartridge being part of a cartridge assembly including a plurality of staples and staple pushers; inserting a distal end of the shipping wedge into a gap between the staple cartridge and the stapling instrument; and manipulating the shipping wedge to separate the staple cartridge from the stapling instrument.

The stapling instrument can include a jaw and the gap can be defined between the staple cartridge and the jaw, the distal end of the shipping wedge being inserted in the gap between the jaw and the staple cartridge. The distal end of the shipping wedge can include a tongue. The tongue of the shipping wedge can be inserted into the gap.

In another aspect, a method of replacing a staple cartridge of a stapling instrument includes separating a shipping wedge from a staple cartridge, the staple cartridge being part of a cartridge assembly including a plurality of staples and staple pushers; inserting a distal end of the shipping wedge into a gap between the staple cartridge and the stapling instrument; manipulating the shipping wedge to separate the staple cartridge from the stapling instrument; and replacing the staple cartridge with an unfired staple cartridge.

In the method, the unfired staple cartridge can have an actuation member with a knife.

DESCRIPTION OF THE DRAWINGS

Various embodiments of the presently disclosed shipping wedge are disclosed herein with reference to the drawings, wherein:

FIG. 2 is a bottom perspective view of the cartridge assembly of FIG. 1;

FIG. 3 is an enlarged view of the area of detail "3" of FIG. 2;

FIG. 17 is a side cross-sectional view of the end effector and shipping wedge of FIG. 10 taken along section line 17-17;

FIG. 18 is an enlarged view of the area of detail "18" of FIG. 17;

DETAILED DESCRIPTION OF THE EMBODIMENTS

Embodiments of the presently disclosed cartridge assembly with a staple cartridge and a shipping wedge will now be described in detail with reference to the drawings wherein like numerals designate identical or corresponding elements in each of the several views. As is common in the art, the term "proximal" refers to that part or component closer to the user or operator, while the term "distal" refers to that part or component farther away from the user or operator.

The presently disclosed cartridge assembly with a staple cartridge and a shipping wedge is usable with endoscopic surgical stapling devices capable of accepting replaceable loading units. An example of such a device is disclosed in U.S. Pat. No. 7,753,246 the entire contents of which are hereby incorporated by reference.

Figure 21:
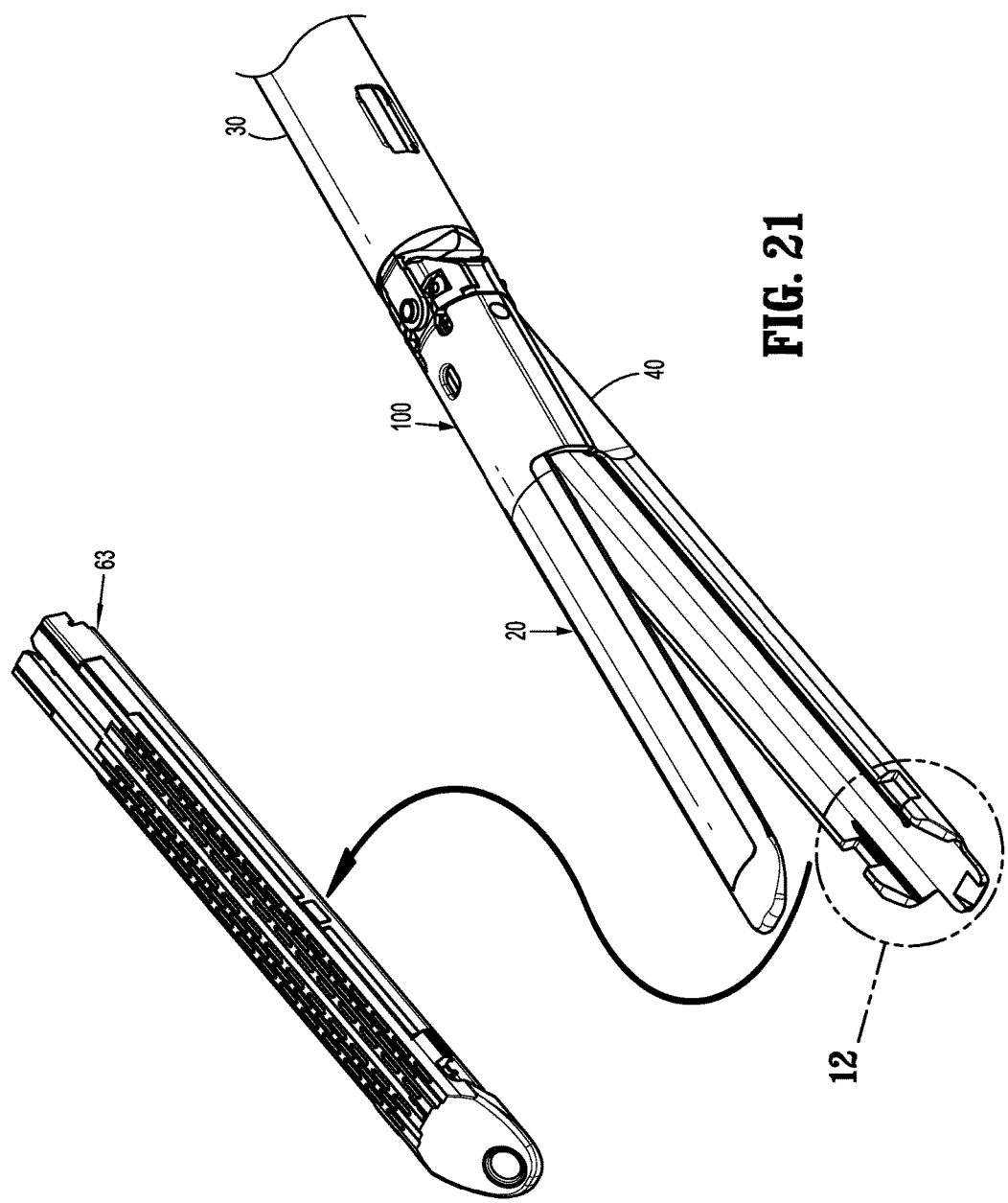
FIG. 21 is a perspective view of the end effector and the staple cartridge assembly without the shipping wedge prior to attaching the staple cartridge assembly to the end effector.
Figure 22:
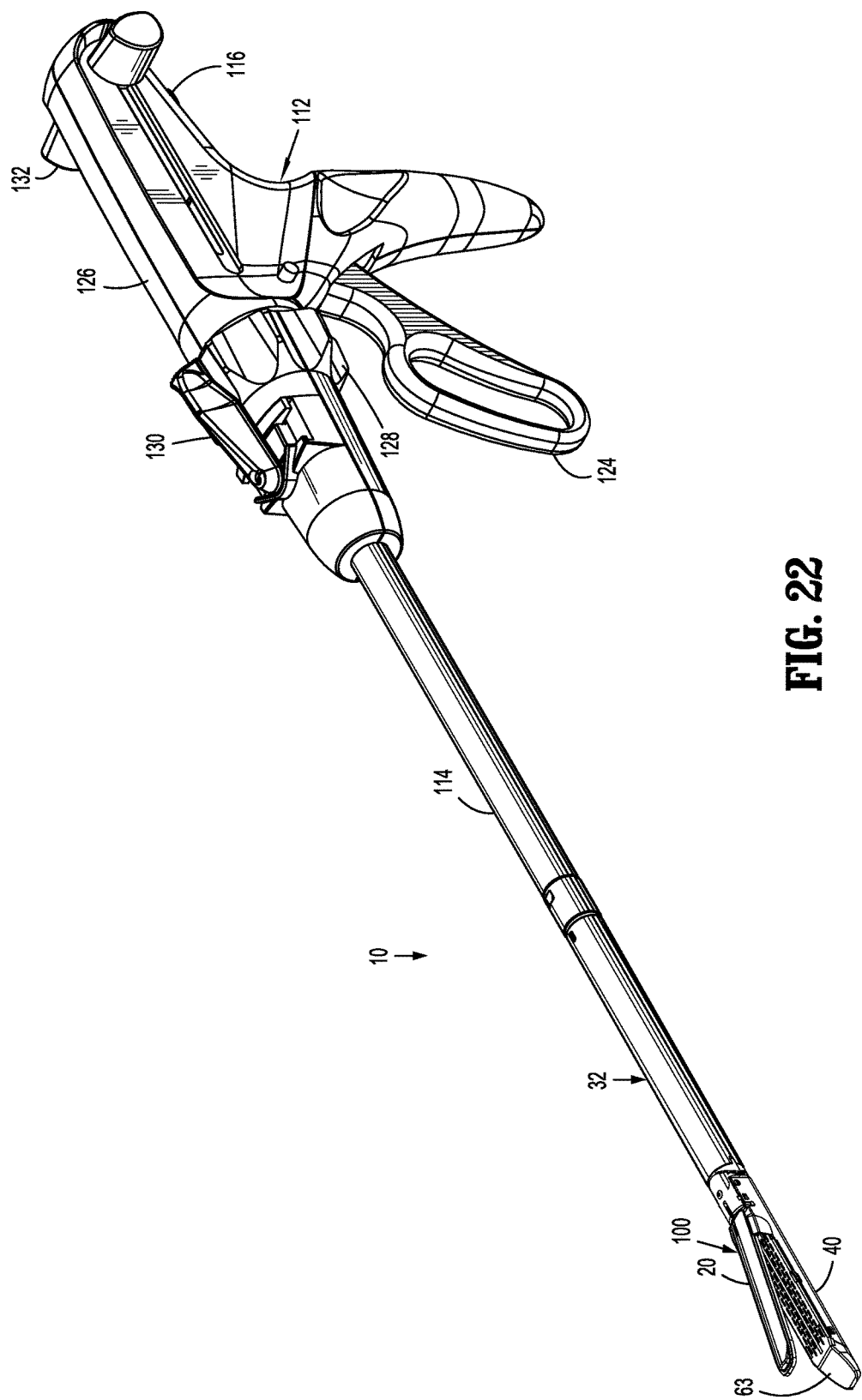
FIG. 22 is a perspective view of a manually operated surgical stapling device according to certain embodiments, that may be used in endoscopic procedures.
Figure 23:
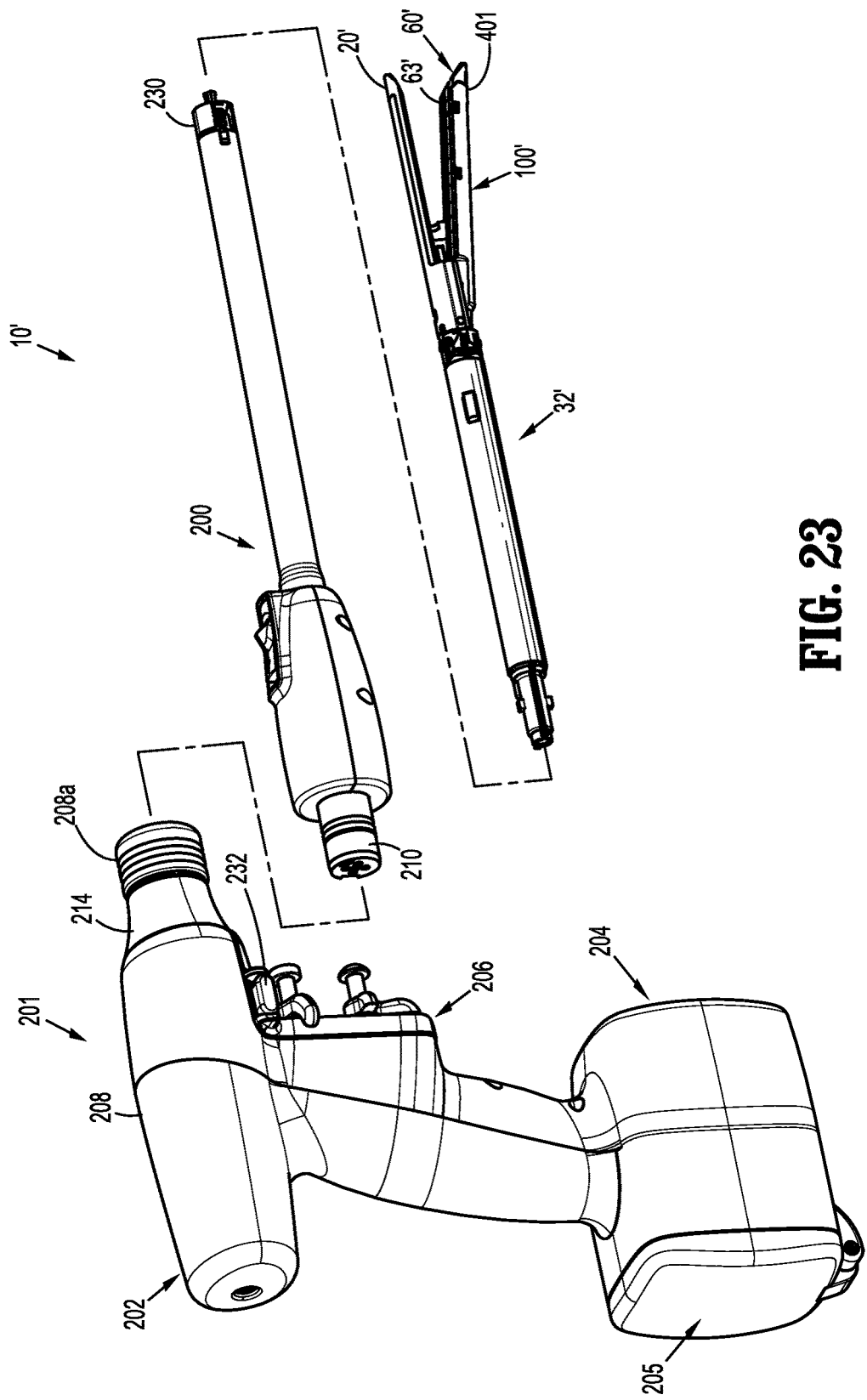
FIG. 23 is perspective view of a powered or motorized surgical device according to certain embodiments, that may be used in endoscopic procedures

An end effector 100 (FIGS. 10 and 21) includes opposing first and second jaws 20, 40 that are pivotably coupled to one another. The end effector 100 can be provided at the distal end of an endoscopic shaft 30 as part of a surgical stapling device, or can form part of a removable and disposable loading unit 32 for a surgical stapling device 10, 10'. FIG. 22 shows a manually operated surgical stapling device 10 that may be used in endoscopic procedures. FIG. 23 shows a powered or motorized surgical stapling device 10' that may be used in endoscopic procedures. Other devices are contemplated, such as other manually operated devices or robotically operated devices.

Figure 12:
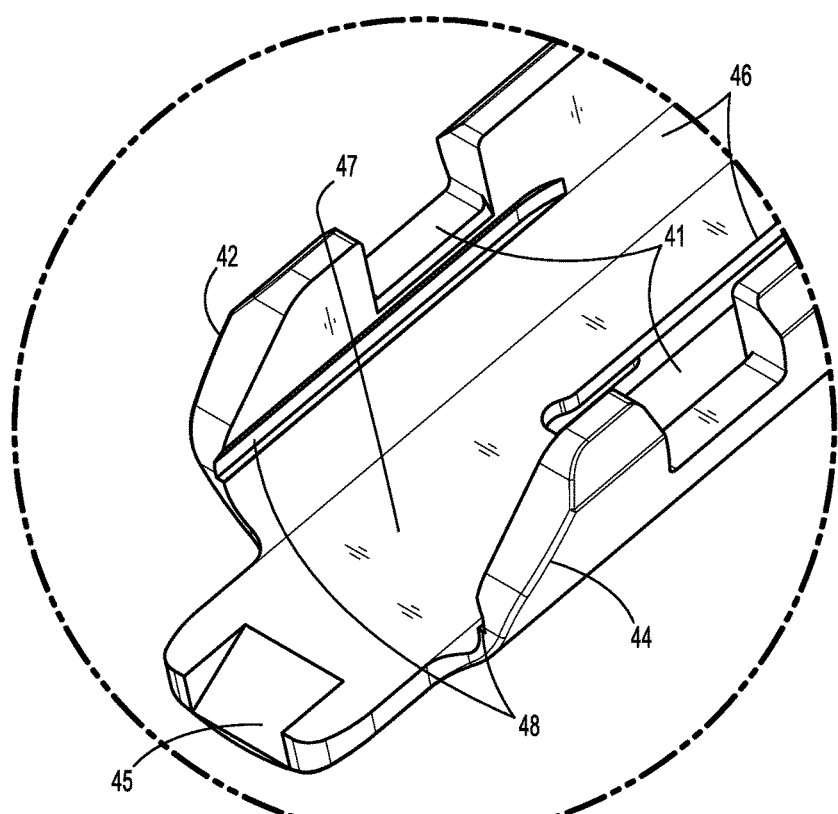
FIG. 12 is an enlarged view of the area of detail "12" of FIG. 21.
Figure 13:
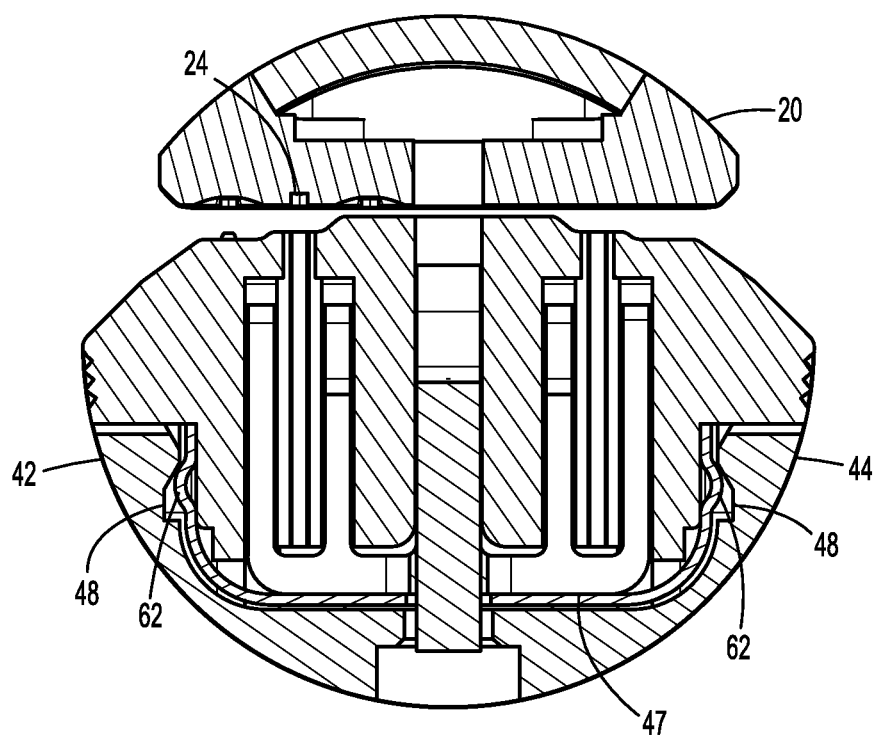
FIG. 13 is an end cross-sectional view of the end effector of FIG. 10 taken along section line 13-13.

The jaws 20, 40 of the end effector 100 are configured for movement between a spaced apart relationship (FIG. 10) and close cooperative alignment (not shown). The first jaw 20 includes a number of rows and each row includes a plurality of staple forming depressions 24 (FIG. 13). The second jaw 40 has opposed sidewalls 42, 44 that define a channel 46 with a generally U-shaped configuration extending between a proximal end of the second jaw 40 and a distal end of the second jaw 40 (FIG. 12). The channel 46 is configured for releasably receiving a staple cartridge 63 that will be described in further detail below. A distal portion of the channel 46 includes recesses 48 disposed on opposing interior surfaces of the channel 46 (FIG. 12). Additionally, the second jaw 40 has notches 41 near its distal end (FIG. 12). Specifically, each notch 41 is generally U-shaped and open at the top for slidably receiving tabs 61 of the staple cartridge 63 as will be later described in further detail. A sloped surface 45 is formed at the distal end of the second jaw member 40 (FIG. 12). The sloped surface 45 extends from the external bottom surface of the jaw member 40 and leads angularly to the interior surface of the jaw member 40.

Figure 1:
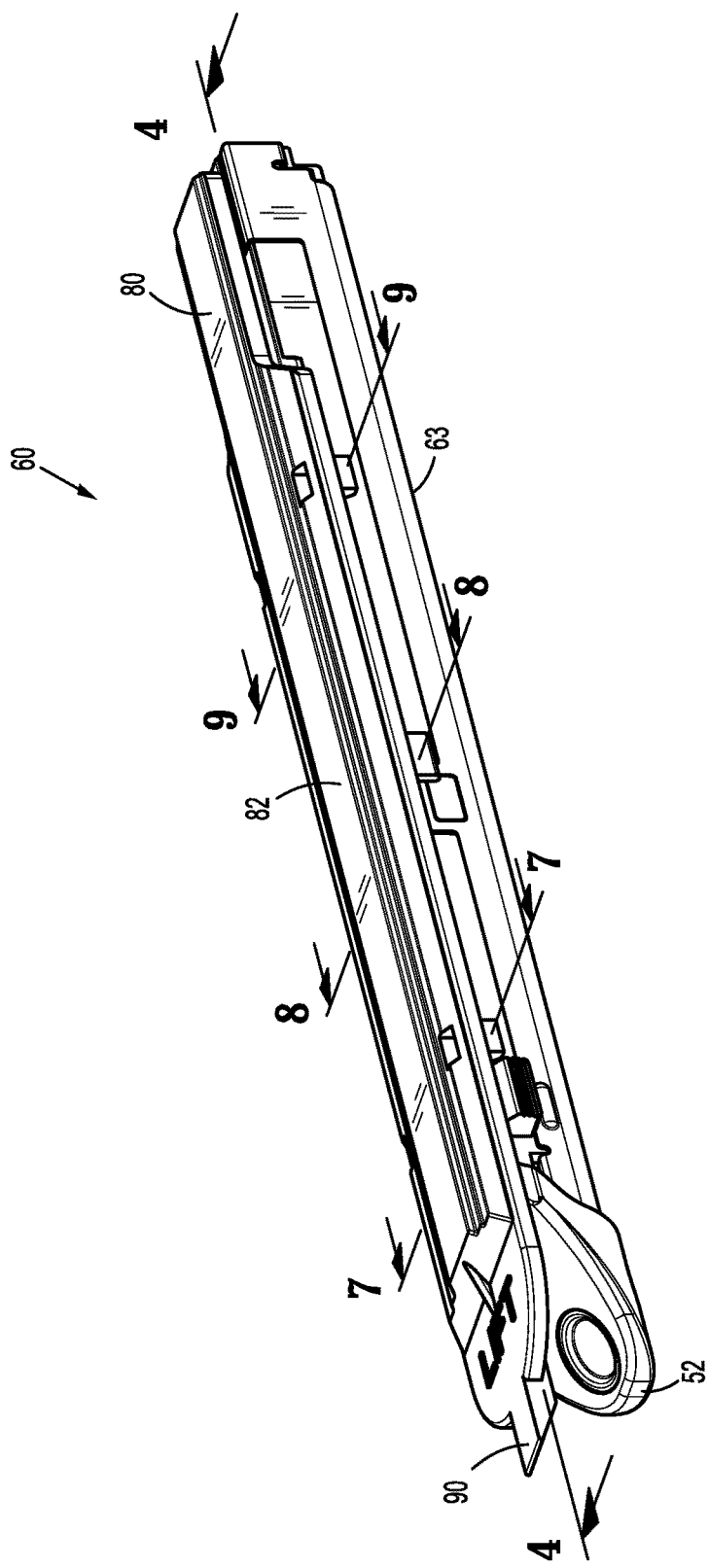
FIG. 1 is a side perspective view of a cartridge assembly including a staple cartridge and a shipping wedge according to an embodiment of the present disclosure.
Figure 4:
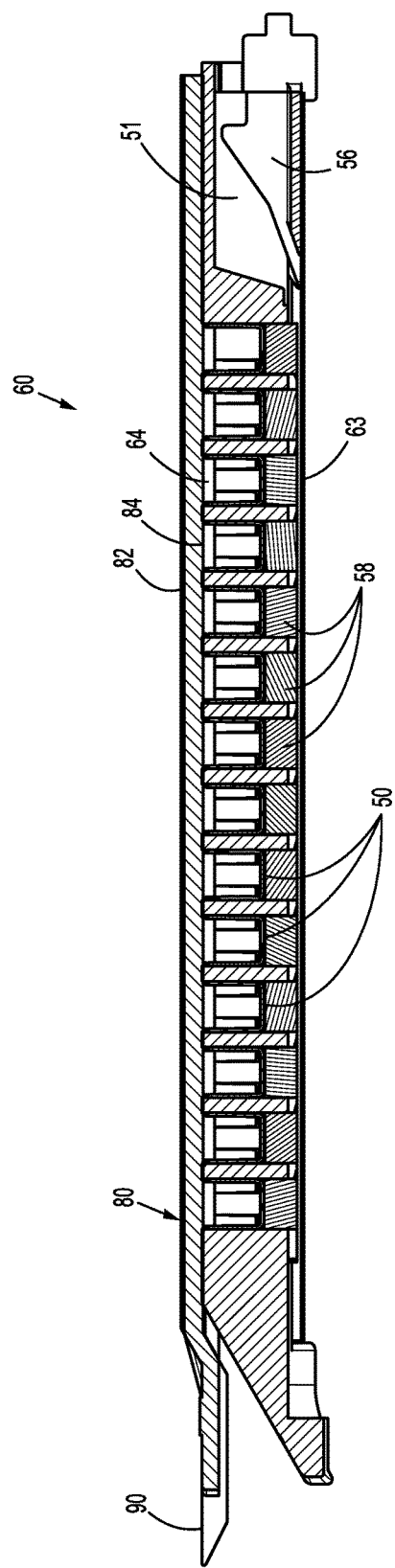
FIG. 4 is a side cross-sectional view of the cartridge assembly of FIG. 1 taken along section line 4-4.
Figure 7:
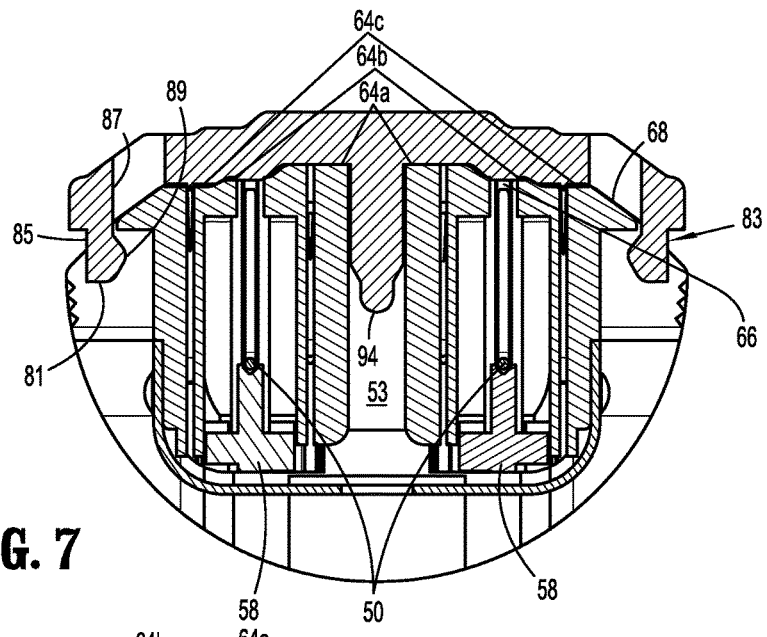
FIG. 7 is an end cross-sectional view of the cartridge assembly of FIG. 1 taken along section line 7-7.

With initial reference to FIGS. 1-3, a replaceable loading unit or cartridge assembly 60 for a surgical stapler, according to the present disclosure, is shown. The cartridge assembly 60 includes a staple cartridge 63 and a shipping wedge 80. The staple cartridge 63 includes retention slots 66 (FIG. 5) for receiving a plurality of staples or fasteners 50 and pushers 58 (FIG. 7). A plurality of laterally spaced apart longitudinal slots extends through the staple cartridge 63 for accommodating upstanding cam wedges of an actuation sled 56 (FIG. 4). A central longitudinal slot extends along substantially the length of staple cartridge 63 and facilitates passage of a drive mechanism (not shown) having an actuation member. The actuation member is advanced by a firing rod and the actuation member abuts the actuation sled 56 and translates the actuation sled 56 through the longitudinal slots of the staple cartridge 63, which advances the cam wedges into sequential contact with the pushers 58. The pushers 58 translate vertically along the cam wedges within the fastener retention slots 66 and urge the fasteners 50 from the retention slots 66 into staple forming depressions 24 (FIG. 13) of the first jaw 20.

Figure 8:
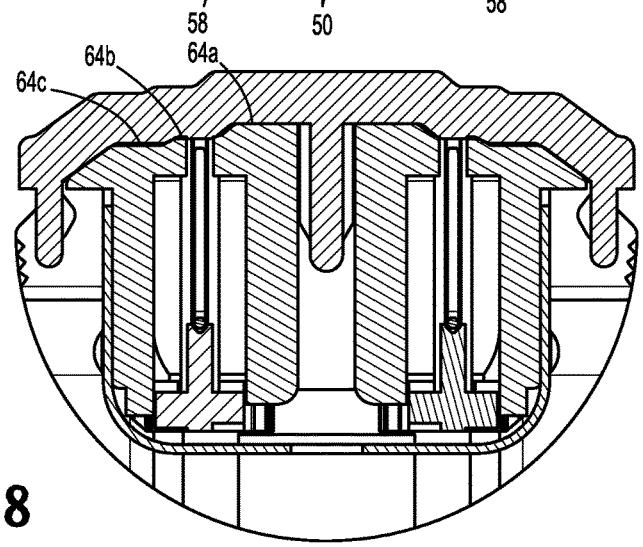
FIG. 8 is an end cross-sectional view of the cartridge assembly of FIG. 1 taken along section line 8-8.
Figure 9:
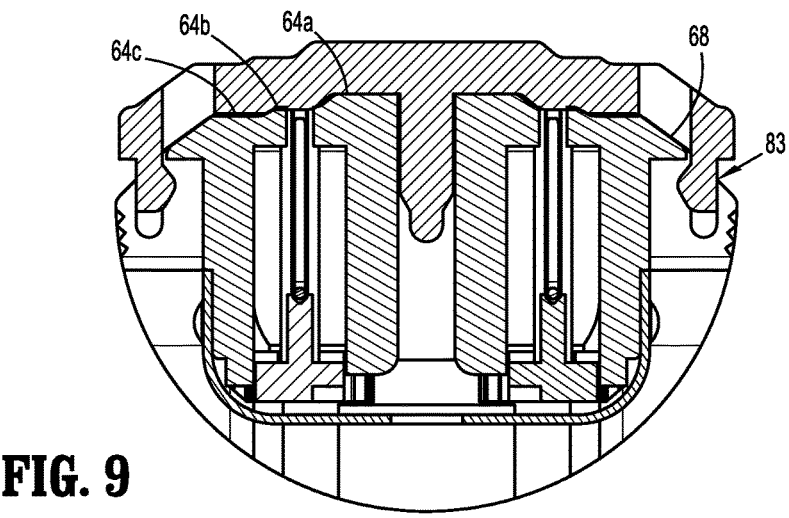
FIG. 9 is an end cross-sectional view of the cartridge assembly of FIG. 1 taken along section line 9-9.
Figure 14:
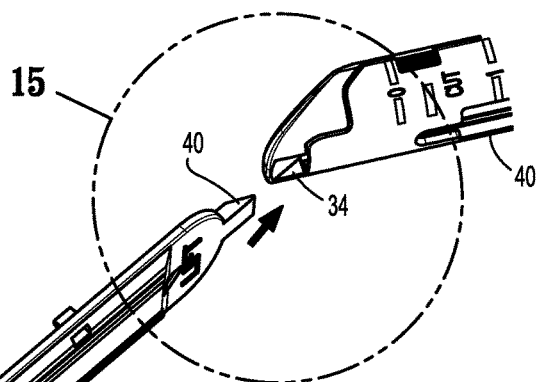
FIG. 14 is a bottom perspective view of the shipping wedge and the staple cartridge prior to separating the staple cartridge from the end effector.
Figure 15:
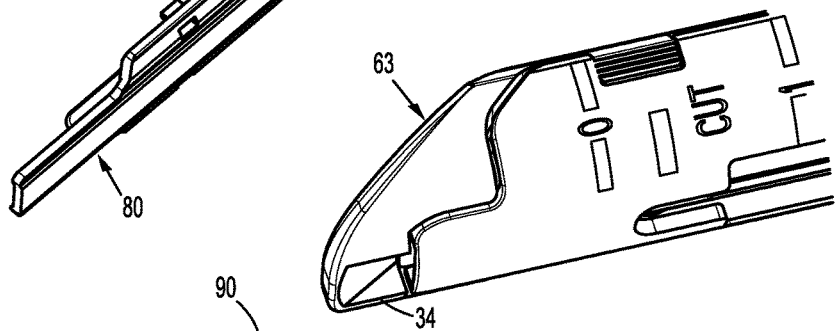
FIG. 15 is an enlarged view of the area of detail "15" of FIG. 14.
Figure 16:
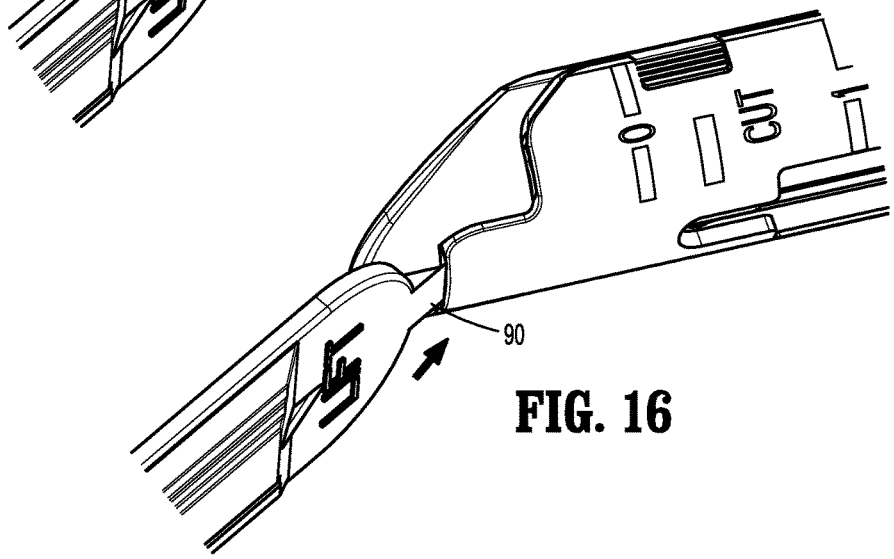
FIG. 16 is an enlarged view of the area of detail "15" of FIG. 14 showing the shipping wedge engaged with the staple cartridge.

The staple cartridge 63 has an elongated body portion that houses a plurality of surgical staples 50 and a plurality of pushers 58 for ejecting the surgical staples 50 from the staple cartridge 63 through openings 67 of the retention slots 66 towards the staple forming depressions 24 on the first jaw 20. The openings 67 extend through a tissue contacting surface 64 of the staple cartridge 63. The tissue contacting surface 64 includes surfaces 64a, 64b, and 64c, forming a stepped shape. As illustrated in FIG. 7, surfaces 64a are located adjacent a knife slot 53 (FIG. 5) that extends from a proximal portion of the staple cartridge 63 to a distal portion of the staple cartridge 60 and is configured for slidably guiding a knife 51 (FIG. 4). Surfaces 64b are positioned adjacent surfaces 64a with surfaces 64c furthest away from the knife slot 53. The surfaces 64a, 64b, and 64c are substantially parallel to one another, but they are located in different planes thereby defining a stepped configuration as seen in FIGS. 7-9. Surfaces 64a are substantially aligned with each other in a first common plane, surfaces 64b are substantially aligned with each other in a second common plane, and surfaces 64c are substantially aligned with each other in a third common plane. The staple cartridge 63 is configured for releasable attachment to the second jaw 40. The elongated body portion of the staple cartridge 63 has an open proximal end for operatively engaging the drive mechanism of the surgical stapling device 10, 10' and a contoured nose 52 disposed at the distal end of the staple cartridge 63 for bluntly engaging body tissue. In particular, the nose 52 has an angled recess 54 disposed on a bottom surface of the nose 52 (FIG. 2). The angled recess 54 of the nose 52 is substantially aligned with the sloped surface 45 of the second jaw member 40 (FIG. 12), thereby defining a gap 34 for receiving a tongue 90 located at a distal end of a shipping wedge 80 (FIGS. 14-16). Each sidewall of the staple cartridge 63 includes an outwardly extending ridge or rail 68, which extends along a major length of each sidewall starting at a distal end of the staple cartridge 63.

In any of the embodiments disclosed herein, the cartridge assembly 60 can include an actuation member with a knife 51, an upper portion for engaging the anvil assembly, and a lower portion for engaging the jaw member 40. An example of such an actuation member is disclosed in U.S. application Ser. No. 13/280,880, the disclosure of which is hereby incorporated by reference herein in its entirety.

Figure 11:
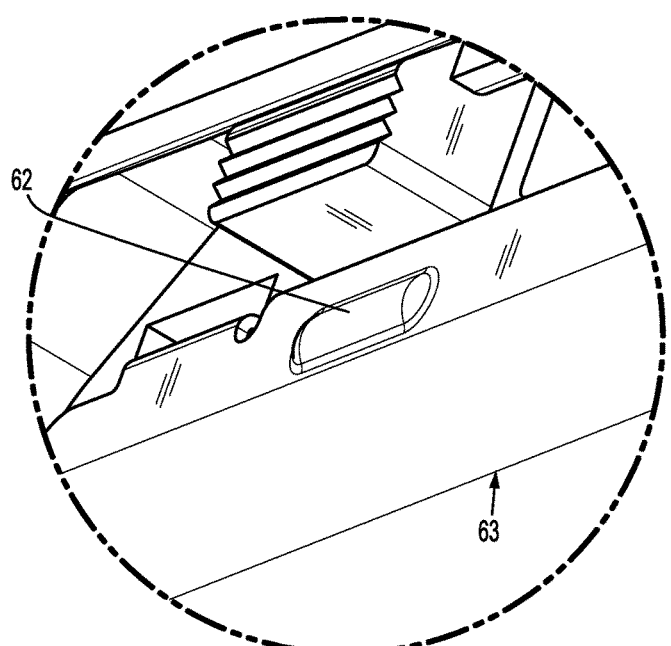
FIG. 11 is an enlarged view of the area of detail "11" of FIG. 2.

Referring to FIGS. 11-13, the staple cartridge 63 includes opposing protrusions 62 near its distal end. The protrusions 62 are configured for frictionally engaging the recesses 48 of the channel 46. Once the staple cartridge 63 is aligned in the channel 46, additional movement of the staple cartridge 63 towards a bottom surface 47 of the channel 46 causes positive engagement of the protrusions 62 and the corresponding recesses 48. Once the staple cartridge 63 is fully seated in the channel 46, the frictional engagement between the protrusions 62 and the recesses 48 maintain the staple cartridge 63 in operational engagement with the channel 46 and the second jaw 40. Further, the staple cartridge 63 includes tabs 61 (FIG. 5) extending from opposite sidewalls of the staple cartridge 63. The tabs 61 are adapted for slidable engagement in the notches 41 of the second jaw 40. When tabs 61 are positioned in the notches 41, the staple cartridge 63 is properly aligned with the channel 46 of the second jaw 40.

Referring to FIGS. 2, 3, 5, and 6, the shipping wedge 80 is releasably attached to the staple cartridge 63. In particular, the shipping wedge 80 is an elongated structure having opposing proximal and distal ends with the tongue 90 extending distally from the distal end. The shipping wedge 80 also includes opposed top and bottom surfaces 82, 84 with the bottom surface 84 configured for contacting the tissue contacting surface 64 of the staple cartridge 63. The shipping wedge 80 has a width that is greater than a width of the staple cartridge 63. A plurality of tabs 83 are disposed on side edges of the shipping wedge 80 and each tab 83 extends in a direction that is transverse to the bottom surface 84 of the shipping wedge 80. Each tab 83 has a generally planar outside surface 85, a generally planar bottom surface 81, and an inner surface 87 with a rounded protrusion 89 opposite the generally planar outside surface 85. Each tab 83 has resilience in that it is bendable with respect to the bottom surface 84 of the shipping wedge 80 and is biased towards a neutral or initial position that is substantially transverse to the bottom surface 84 of the shipping wedge 80. Additionally, the shipping wedge 80 includes a central keel 94 that extends along a major portion of the bottom surface 84 of the shipping wedge 80. The keel 94 is configured for positioning in the knife slot 53 of the staple cartridge 63. The shipping wedge 80 and the staple cartridge 63 are releasably attached to each other as described below.

Figure 5:
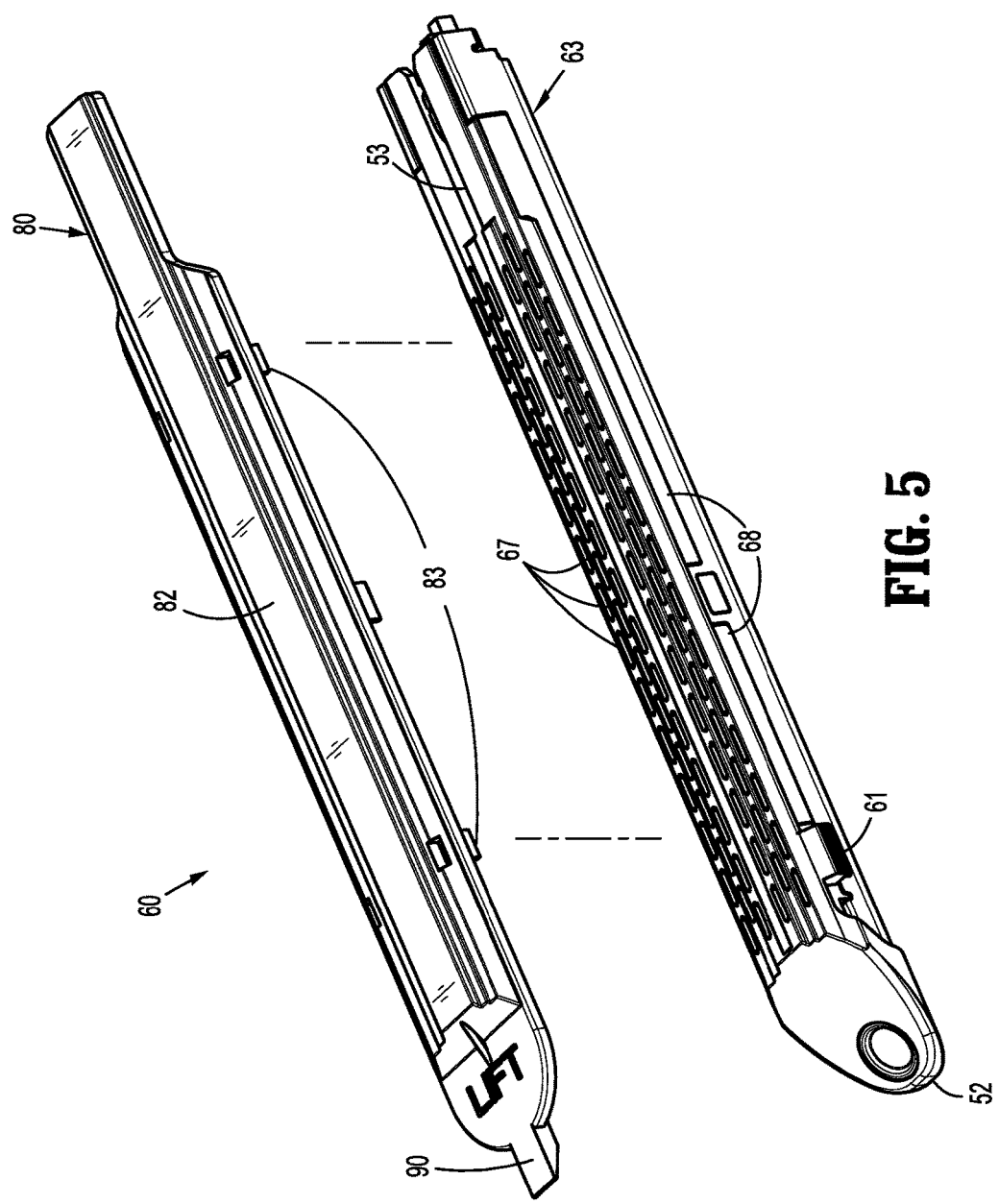
FIG. 5 is an exploded perspective view of the cartridge assembly of FIG. 1 with parts separated.

As best illustrated in FIG. 5, the shipping wedge 80 is initially separated from the staple cartridge 63 and oriented such that the bottom surface 84 of the shipping wedge 80 is in opposition with the tissue contacting surface 64 of the staple cartridge 63. As the shipping wedge 80 is advanced into engagement with the staple cartridge 63, the tabs 83 of the shipping wedge 80 engage the rails 68 of the staple cartridge 63. The resiliency of the tabs 83 allows them to flex outwardly and away from the longitudinal axis of the shipping wedge 80 as the shipping wedge 80 is attached to the staple cartridge 63. This is assisted by the curvate configuration of the protrusion 89 on the inner surface 87 of the tab 83. With the bottom surface of the shipping wedge 84 in contact with the tissue contacting surface 64 of the staple cartridge 63, the curvate protrusions 89 of the tabs 83 are no longer in contact with the rails 68 of the staple cartridge 63. In particular, as seen in FIG. 7, the configuration of the rails 68 and the tabs 83 of the shipping wedge 80 is such that when the shipping wedge 80 is seated on the tissue contacting surface 64 of the staple cartridge 63, the curvate protrusion 89 of each tab 83 has traversed beyond the rail 68. Since each tab 83 is resiliently biased towards the neutral position, when the curvate protrusion 89 has traversed beyond the rail, the tab 83 returns to its neutral position aided by the resiliency of the tab and an upper portion of the curvate protrusion 89 engages an edge of the rail 68 and holds the shipping wedge 80 in place with the staple cartridge 63. The central keel 94, in cooperation with the knife slot 53, acts to align the shipping wedge 80 with the staple cartridge 63. Further still, when the shipping wedge 80 is attached to the staple cartridge, the bottom surface 84 of the shipping wedge 80 abuts the tissue contacting surface 64 of the staple cartridge 63 and maintains the surgical staples 50 in their respective retention slots 66. Further still, the bottom surface 84 of the shipping wedge 80 has a complementary configuration to that of the tissue contacting surface 64 of the staple cartridge 63. For example, the bottom surface 84 of the shipping wedge 80 may have a stepped shape to correspond to the stepped shape of the tissue contacting surface. The shipping wedge 80 may also maintain a uniform distance between the first and second jaws 20, 40 when the jaws 20, 40 are in close cooperative alignment.

Figure 10:
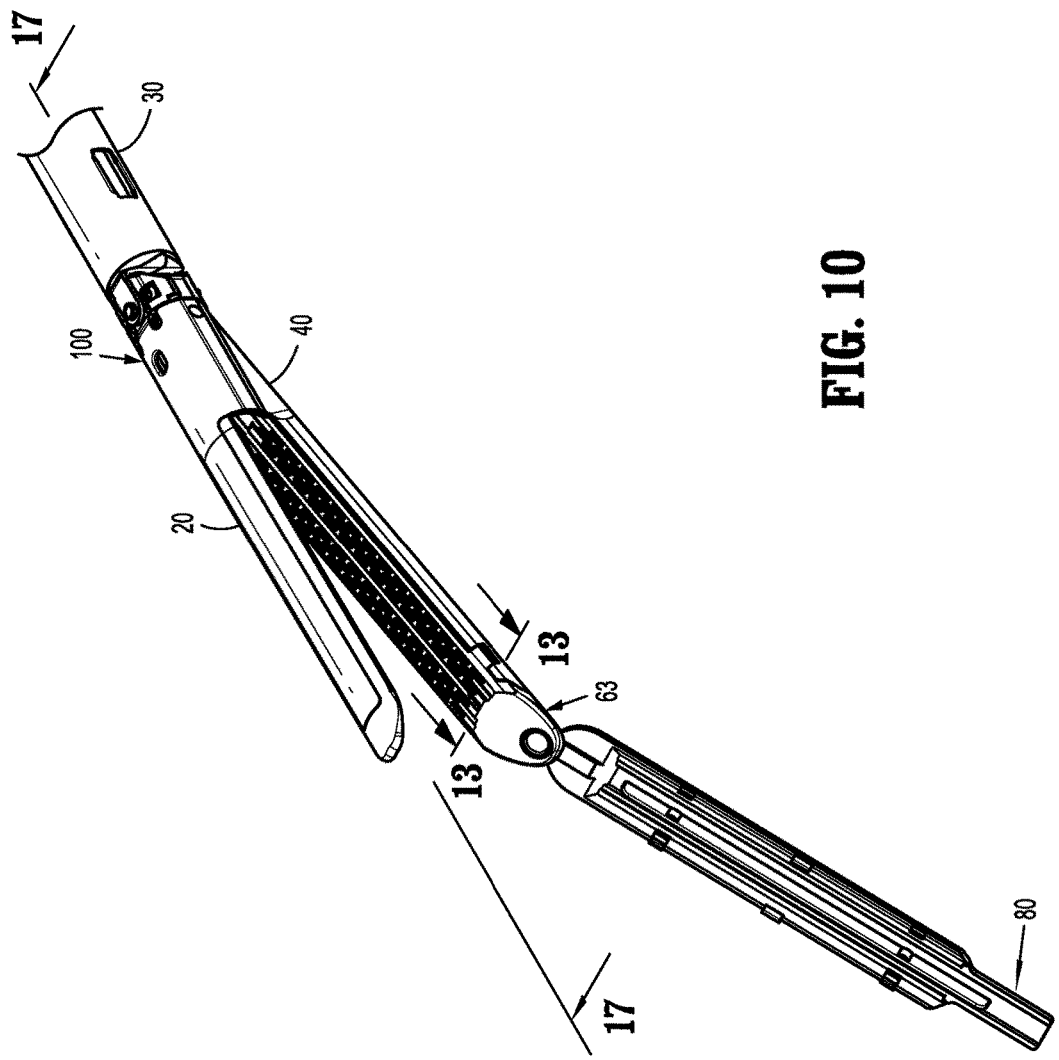
FIG. 10 is a perspective view of an end effector with the cartridge assembly of FIG. 1 showing the shipping wedge used as a release tool for the staple cartridge.
Figure 19:
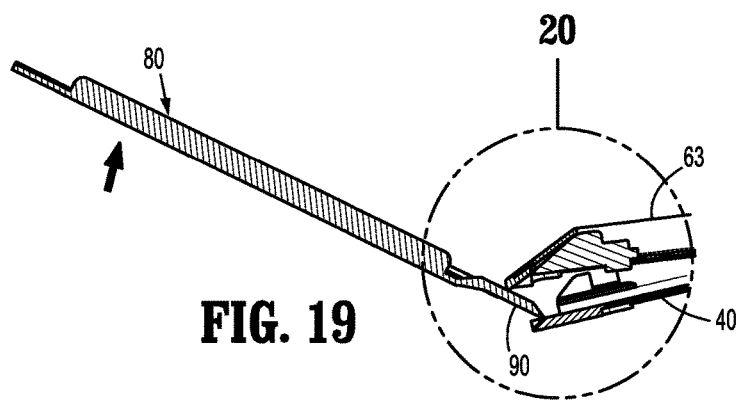
FIG. 19 is an enlarged view of the end effector and shipping wedge of FIG. 17 showing the shipping wedge separating the staple cartridge from the end effector.
Figure 20:
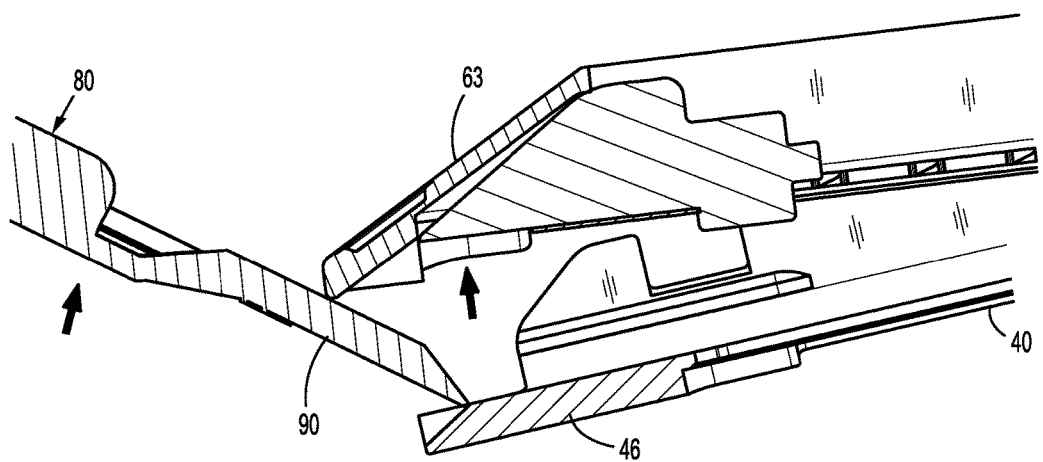
FIG. 20 is an enlarged view of the area of detail "20" of FIG. 19.

Referring now to FIG. 10, the first and second jaws 20, 40 are spaced apart and the shipping wedge 80 has been separated from the staple cartridge 63 of the cartridge assembly 60. In particular, the shipping wedge 80 is positioned such that the tongue 90 is inserted into the gap 34 between the staple cartridge 63 and the channel 46 of the second jaw 40. With additional reference to FIGS. 14-18, removal of the staple cartridge 63 from the second jaw 40 will now be described. The shipping wedge 80 is oriented such that the top surface 82 of the shipping wedge 80 is facing the same direction as the bottom surface 47 of the second jaw 40 of the end effector 100. With this arrangement, the tongue 90 of the shipping wedge 80 is readily insertable into the gap 34 between the staple cartridge 63 and the second jaw 40 as shown in FIGS. 15-18. With the tongue 90 of the shipping wedge 80 disposed in the gap 34 between the staple cartridge 60 and the second jaw 40, the shipping wedge 80 is manipulated relative to the second jaw 40, as shown in FIGS. 19 and 20. For example, the shipping wedge 80 is pivoted with a distal tip of the tongue 90 acting as a pivot point for the shipping wedge 80. As the shipping wedge 80 is pivoted relative to the second jaw 40, contact between a bottom surface of the tongue 90 and a distal portion of the staple cartridge 63 applies sufficient force and overcomes the frictional engagement between the protrusions 62 of the staple cartridge 63 and the recesses 48 of the channel 46 of the second jaw 40. Thus, the staple cartridge 63 is separated from the channel 46 of the second jaw 40 as shown in FIGS. 19 and 20. After the staple cartridge 63 is separated from the channel 46 of the second jaw 40, a replacement cartridge may be inserted into the channel 46 and operatively coupled to the surgical instrument.

The shipping wedge 80 maintains the staples in the cartridge assembly 60, and facilitates the removal of the cartridge assembly 60 from the second jaw 40 while minimizing the user's potential contact with the knife 51. Furthermore, in any of the embodiments disclosed herein, the shipping wedge 80 can be configured to shield or cover the blade of the knife 51 or some other portion of the actuation member.

Figure 6:
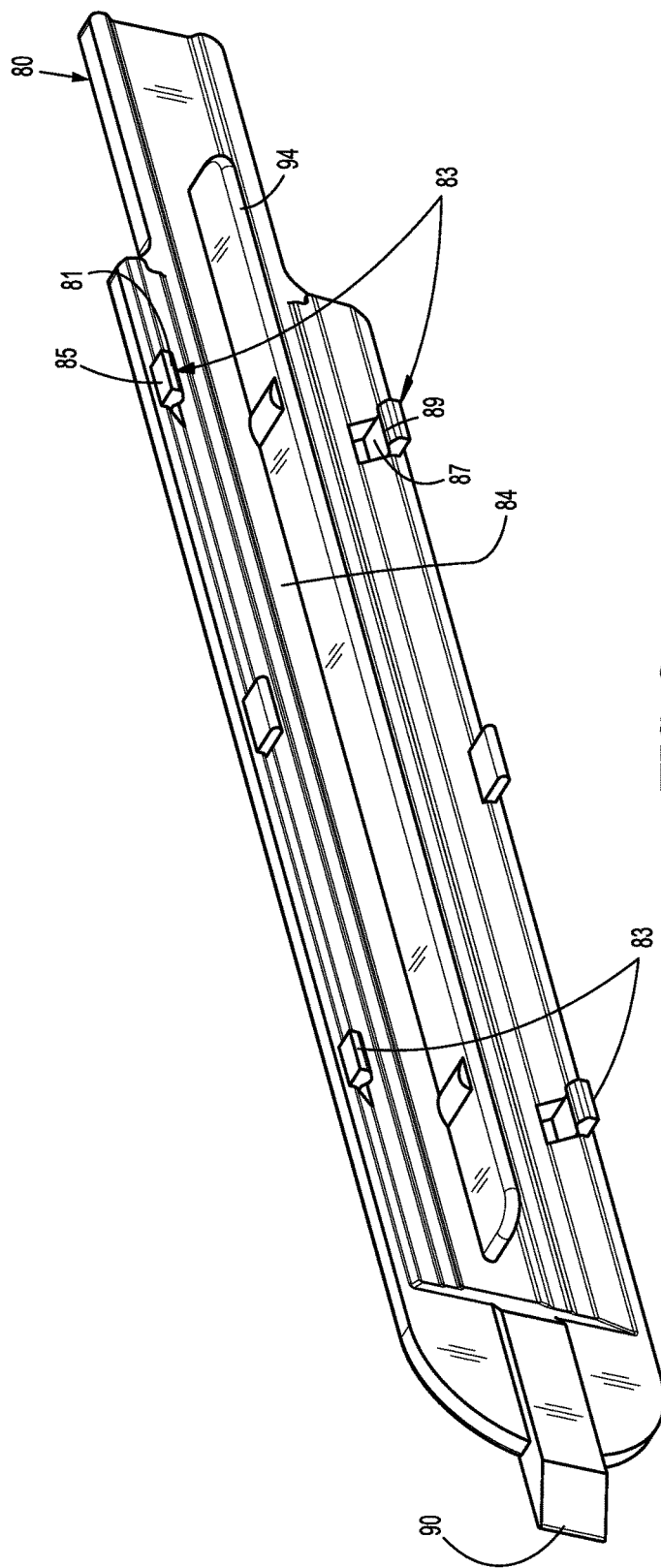
FIG. 6 is a bottom perspective view of the shipping wedge of FIG. 1.
Figure 6A:
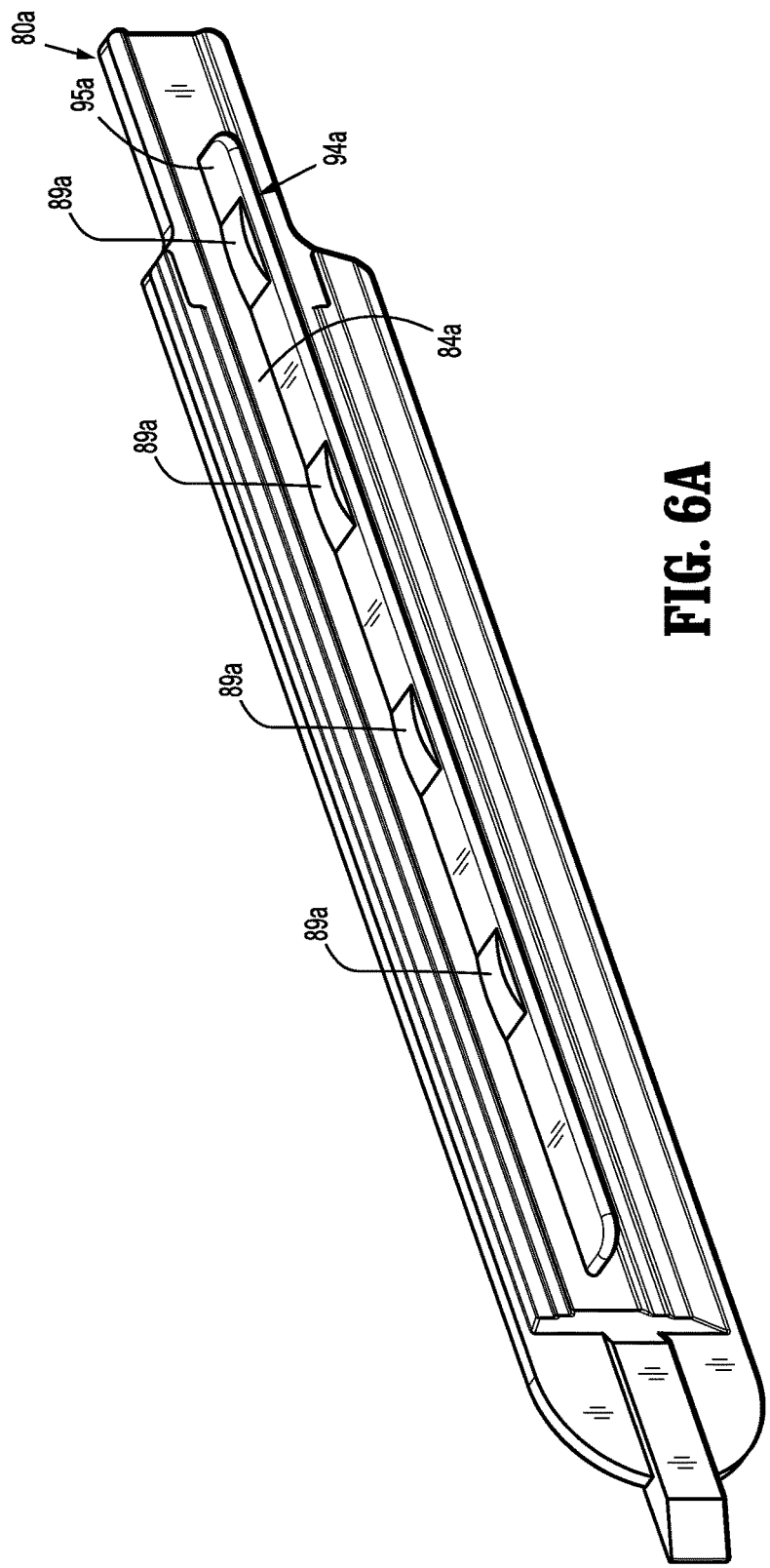
FIGS. 6A and 6B are bottom perspective views of other shipping wedges according to embodiments of the present disclosure.
Figure 6B:
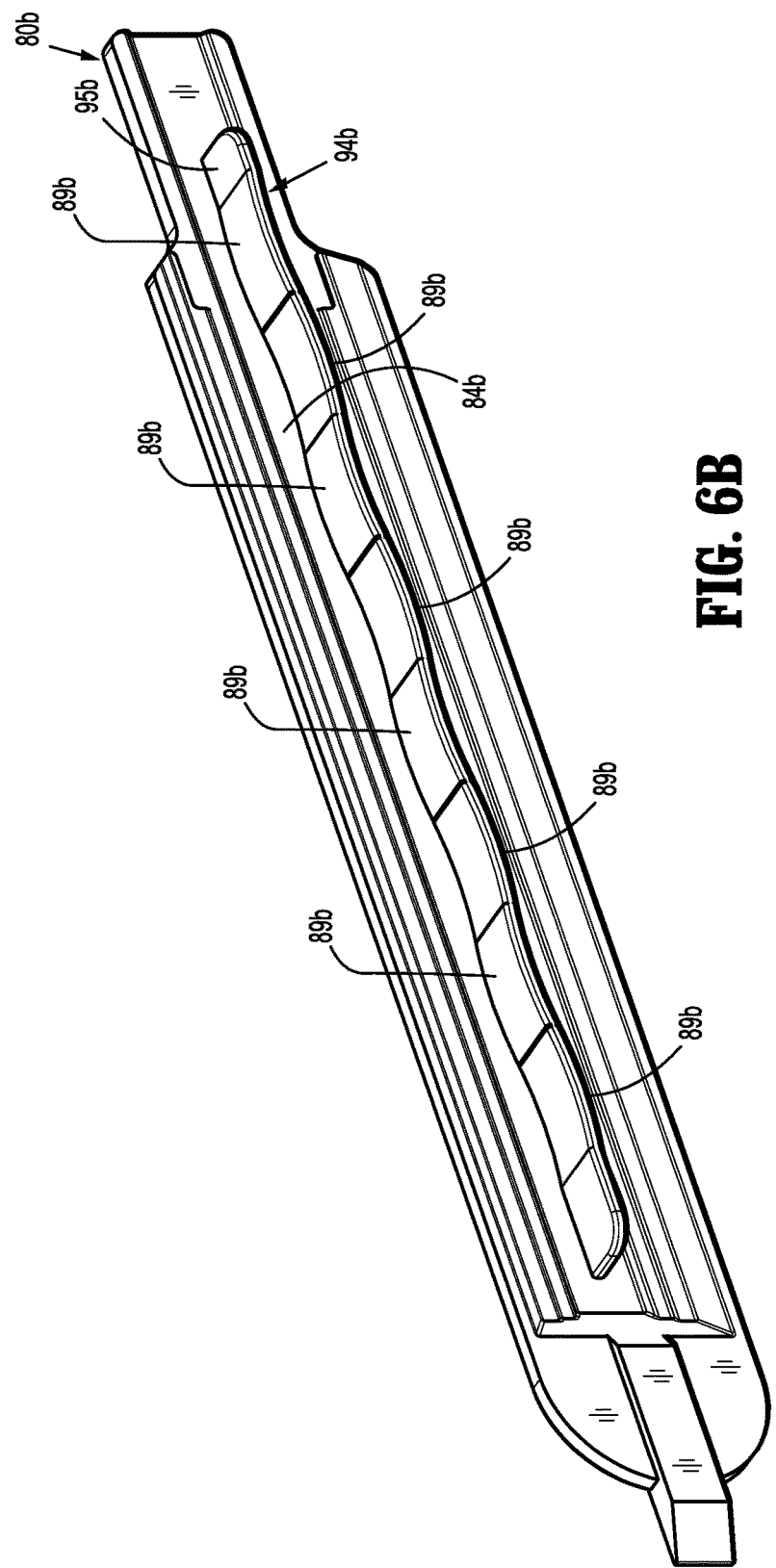

With reference to FIGS. 6A and 6B, additional embodiments of the shipping wedge are disclosed. Each shipping wedge is substantially similar to shipping wedge 80 and only the differences are discussed in detail. FIG. 6A illustrates a shipping wedge 80a including a central keel 94a that extends along a major portion of a bottom surface 84a of shipping wedge 80b. Central keel 94a has side surfaces 95a. Each side surface 95a includes a plurality of curved protrusions 89a. When shipping wedge 80a is attached to staple cartridge 60, the plurality of curved protrusions 89a cooperate with knife slot 53 to align shipping wedge 80a with staple cartridge 63 and attach shipping wedge 80a to staple cartridge 63 with a friction fit. The plurality of curved protrusions 89a can align shipping wedge 80a longitudinally and/or centrally with staple cartridge 63.

Now referring to FIG. 6B, a shipping wedge 80b includes a central keel 94b that extends along a major portion of a bottom surface 84b of shipping wedge 80b. Central keel 94b includes side surfaces 95b forming a wave pattern about the longitudinal axis. The wave pattern has a plurality of crests or curved protrusions 89b. When shipping wedge 80b is attached to staple cartridge 60, the plurality of curved protrusions 89b cooperate with knife slot 53 to align shipping wedge 80b with staple cartridge 63 and attach shipping wedge 80b to staple cartridge 63 with a friction fit. The plurality of curved protrusions 89b can align shipping wedge 80b longitudinally and/or centrally with staple cartridge 63.

Referring now to FIG. 22, a manually operated surgical stapling device 10 is disclosed, an example of such a device is disclosed in U.S. Pat. No. 7,565,993 the entire contents of which is hereby incorporated by reference. Briefly, manually operated surgical stapling device 10 includes a handle assembly 112 and an elongated body 114. A disposable loading unit or DLU 32 is releasably secured to a distal end of elongated body 114. Disposable loading unit 32 includes an end effector 100 having a first jaw 20 and a second jaw 40. The second jaw 40 is configured to releasably receive a staple cartridge 63 of a cartridge assembly 60, as described above. Handle assembly 112 includes a stationary handle member 122, a movable handle member 124, and a barrel portion 126. Handle assembly 112 actuates a drive mechanism (not shown) having a firing rod that advances the actuation member abutting the actuation sled 56 (FIG. 4), as discussed above, when the moveable handle member 124 is moved towards the stationary handle member 122. Handle assembly 112 may also actuate first and second jaws 20, 40 from the spaced apart relationship to the close cooperative alignment.

FIG. 23 illustrates an exemplary embodiment of a powered or motorized surgical stapling device 10', an example of such a device is disclosed in U.S. patent application Ser. No.

13/331,047 the disclosure of which is hereby incorporated by reference herein in its entirety. Powered surgical stapling device 10' includes a handle 201, an adaptor 200, and a disposable loading unit 32'. Handle 201 includes a handle housing 202 having a lower housing portion 204, an intermediate housing portion 206 extending from and/or supported on lower housing portion 204, an upper housing portion 208 extending from and/or supported on intermediate housing portion 206, and a cavity (not shown) defined within. A drive mechanism (not shown) is situated within the cavity. The drive mechanism may be disposed within the upper portion 208. A connecting portion 208a of upper housing portion 208 is configured to accept a corresponding drive coupling assembly 210 of adapter 200. An end effector coupling assembly 230 at the distal end of adaptor 200 is configured to receive the proximal end of disposable loading unit 32'. When adapter 200 is mated to handle 201 and disposable loading unit 32', the drive mechanism engages a firing rod that advances the actuation member abutting the actuation sled 56 (FIG. 4), as discussed above, when a button of button assembly 232 is depressed. Button assembly 232 may also include a button that actuates first and second jaws 20, 40 from the spaced apart relationship to the close cooperative alignment.

In another aspect, a method of removing a staple cartridge from a stapling instrument includes separating a shipping wedge from a staple cartridge, inserting a distal end of the shipping wedge into a gap between the staple cartridge and the stapling instrument, and manipulating the shipping wedge to separate the staple cartridge from the stapling instrument. Any of the embodiments of the cartridge assembly 60 including the staple cartridge 63 and the shipping wedge 80, 80a, 80b and a surgical stapling device 10, 10', disclosed herein, can be used with the method.

The step of separating a shipping wedge may include grasping a tongue on the distal end of the shipping wedge and grasping a nose on the distal end of the staple cartridge and pulling the tongue and the nose in opposing directions. The shipping wedge and staple cartridge may be part of a cartridge assembly. The stapling instrument may include a jaw and the gap may be defined between the staple cartridge and the jaw. The step of inserting may include inserting the tongue into the gap. Manipulating the shipping wedge may include pivoting the shipping wedge with respect to the gap, thus overcoming the frictional engagement between the staple cartridge and the stapling instrument.

In a further aspect, a method of replacing a staple cartridge of a stapling instrument is disclosed. The method includes removing the staple cartridge from a stapling instrument and replacing the staple cartridge with a new or unfired cartridge assembly. The method includes the steps of separating a shipping wedge from a staple cartridge, inserting a distal end of the shipping wedge into a gap, manipulating the shipping wedge to separate the staple cartridge from the stapling instrument, and inserting an unfired staple cartridge into the stapling instrument. The method may include any of the embodiments of the cartridge assembly 60 including the staple cartridge 63 and the shipping wedge 80, 80a, 80b and a surgical stapling device 10, 10'. The method may also include any of the embodiments of the method for removing a staple cartridge from a stapling instrument disclosed herein.

In some embodiments, the unfired staple cartridge includes an actuation member with a knife.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
a first jaw pivotably coupled to a second jaw, the second jaw having a channel;
a staple cartridge positioned in the channel, the staple cartridge and the second jaw defining a gap therebetween; and
a shipping wedge releasably attached to the staple cartridge, the shipping wedge having a tongue extending from one end thereof, the tongue insertable into the gap when the staple cartridge is positioned in the channel such that manipulating the shipping wedge separates the staple cartridge from the second jaw.

2. The surgical instrument of claim 1, wherein the tongue has a tapered configuration and the second jaw has a recess for receiving the tongue.

3. The surgical instrument of claim 1, wherein the second jaw has a generally U-shaped configuration with opposing sidewalls, each sidewall defining a groove extending along a portion of its length, each groove configured to receive a portion of the staple cartridge to secure the staple cartridge within the channel.

4. The surgical instrument of claim 1, wherein the shipping wedge includes a plurality of tabs and the staple cartridge including rails, each rail extending along a portion of a length of the staple cartridge, each tab configured for releasably engaging one of the rails of the staple cartridge.

5. The surgical instrument of claim 1, wherein the shipping wedge maintains a uniform distance between the first and second jaws when the jaws are in a close cooperative alignment.

6. The surgical instrument of claim 1, wherein the shipping wedge includes a keel disposed in a channel of the staple cartridge.

7. The surgical instrument of claim 6, wherein the keel aligns the shipping wedge and the staple cartridge.

8. The surgical instrument of claim 6, wherein the keel inhibits translation of an actuation member through the channel.

9. The surgical instrument of claim 1, wherein the shipping wedge maintains surgical fasteners in their respective retention slots.

10. The surgical instrument of claim 1, wherein the staple cartridge includes opposed sidewalls, each sidewall having a knob extending therefrom, the knobs receivable in recesses formed in a distal portion of the second jaw.

11. The surgical instrument of claim 10, wherein the engagement of the knobs and the recesses maintains the staple cartridge in the second jaw.

12. The surgical instrument of claim 1, wherein the gap is defined between a distal portion of the staple cartridge and a distal portion of the second jaw member.

13. The surgical instrument of claim 1, wherein a sloped surface is formed at a distal end of the second jaw member.

14. The surgical instrument of claim 13, wherein the sloped surface extends from an external bottom surface of the second jaw member and leads angularly to an interior surface of the second jaw member.

15. The surgical instrument of claim 1, wherein the shipping wedge has a stepped shape.

16. A method of removing a cartridge assembly from a stapling instrument, comprising:

separating a shipping wedge from a staple cartridge, the staple cartridge being part of a cartridge assembly including a plurality of staples and staple pushers;

inserting a distal end of the shipping wedge into a gap between the staple cartridge and the stapling instrument when the staple cartridge is coupled to the stapling instrument; and manipulating the distal end of the shipping wedge within the gap to separate the staple cartridge from the stapling instrument.

17. The method according to claim 16, wherein inserting the distal end of the shipping wedge into the gap includes inserting the distal end of the shipping wedge between a jaw of the stapling instrument and the staple cartridge.

18. The method according to claim 16, wherein inserting the distal end of the shipping wedge into the gap includes inserting a tongue of the shipping wedge into the gap.

19. A method of replacing a staple cartridge of a stapling instrument, comprising:

separating a shipping wedge from a staple cartridge, the staple cartridge and shipping wedge being part of a cartridge assembly including a plurality of staples and staple pushers;

inserting a distal end of the shipping wedge into a gap between the staple cartridge and the stapling instrument when the staple cartridge is coupled to the stapling instrument;

manipulating the distal end of the shipping wedge within the gap to separate the staple cartridge from the stapling instrument; and replacing the staple cartridge with an unfired staple cartridge.

20. The method according to claim 19, wherein the unfired staple cartridge includes an actuation member having a knife.

* * * * *

UNITED STATES PATENT AND TRADEMARK OFFICE
CERTIFICATE OF CORRECTION

PATENT NO. : 9,706,993 B2  Page 1 of 1
APPLICATION NO. : 14/159012
DATED : July 18, 2017
INVENTOR(S) : Hessler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this
Twenty-fifth Day of September, 2018

Andrei Iancu
*Director of the United States Patent and Trademark Office*